(12) United States Patent
Schneider et al.

(10) Patent No.: US 10,433,916 B2
(45) Date of Patent: Oct. 8, 2019

(54) SYSTEM AND METHOD FOR DETERMINING THE POSITION AND ORIENTATION OF A TOOL TIP RELATIVE TO EYE TISSUE OF INTEREST

(71) Applicant: Elbit Systems Ltd., Haifa (IL)

(72) Inventors: Ron Schneider, Haifa (IL); Abraham Zeitouny, Haifa (IL); Einav Namer Yelin, Haifa (IL)

(73) Assignee: Elbit Systems Ltd., Haifa (IL)

( * ) Notice: Subject to any disclaimer, the term of this patent is extended or adjusted under 35 U.S.C. 154(b) by 0 days.

(21) Appl. No.: 16/066,480

(22) PCT Filed: Dec. 22, 2016

(86) PCT No.: PCT/IL2016/051370
§ 371 (c)(1),
(2) Date: Jun. 27, 2018

(87) PCT Pub. No.: WO2017/115352
PCT Pub. Date: Jul. 6, 2017

(65) Prior Publication Data
US 2019/0000563 A1    Jan. 3, 2019

(30) Foreign Application Priority Data
Dec. 28, 2015 (IL) .......................................... 243384

(51) Int. Cl.
*A61B 5/05* (2006.01)
*A61B 34/20* (2016.01)
(Continued)

(52) U.S. Cl.
CPC ............ *A61B 34/20* (2016.02); *A61B 3/0008* (2013.01); *A61B 3/10* (2013.01); *A61B 5/0033* (2013.01);
(Continued)

(58) Field of Classification Search
CPC .......... A61B 34/10; A61B 34/20; A61B 34/25
See application file for complete search history.

(56) References Cited

U.S. PATENT DOCUMENTS

| 8,945,140 B2 | 2/2015 | Hubschman et al. |
| 2007/0171369 A1* | 7/2007 | Grundig ............... A61B 3/0025 351/210 |
| 2010/0324542 A1* | 12/2010 | Kurtz ..................... A61F 9/008 606/6 |
| 2011/0213342 A1 | 9/2011 | Tripathi et al. |

(Continued)

OTHER PUBLICATIONS

International Search Report and Written Opinion dated Apr. 2, 2017 for International Application No. PCT/IL2016/051370 (9 Pages).
(Continued)

*Primary Examiner* — Joel F Brutus
(74) *Attorney, Agent, or Firm* — Brown Rudnick LLP (57) ABSTRACT

System and method for determining the position and orientation (P&O) of a tool-tip relative to an eye tissue of interest. The system includes and imaging and tracking module coupled with a processor. The imaging and tracking module at least includes an imager. The imager acquires at least one image of at least one tissue-reference-marker. The imaging and tracking module further determines information relating to the P&O of the tool. The processor determines the P&O of the tissue-reference-marker according to the acquired image of the tissue-reference-marker. The processor determines the P&O of the eye tissue of interest, according to the P&O of the tissue-reference-marker, and a predetermined relative P&O between the tissue-reference-marker and the eye tissue of interest. The processor also determines the P&O of a tool-tip according to a tool-marker and determines the relative P&O between the tool-tip and the eye tissue of interest.

19 Claims, 6 Drawing Sheets

(51) Int. Cl.
| | |
|---|---|
| *A61B 3/10* | (2006.01) |
| *A61B 5/00* | (2006.01) |
| *A61B 5/06* | (2006.01) |
| *A61B 34/10* | (2016.01) |
| *A61B 34/00* | (2016.01) |
| *A61B 90/35* | (2016.01) |
| *G06T 7/73* | (2017.01) |
| *A61B 3/00* | (2006.01) |
| *A61F 9/007* | (2006.01) |

(52) U.S. Cl.
CPC ............ *A61B 5/0077* (2013.01); *A61B 5/061* (2013.01); *A61B 5/064* (2013.01); *A61B 34/10* (2016.02); *A61B 34/25* (2016.02); *A61B 90/35* (2016.02); *G06T 7/74* (2017.01); *A61B 5/6844* (2013.01); *A61B 2034/104* (2016.02); *A61B 2034/105* (2016.02); *A61B 2034/2057* (2016.02); *A61B 2034/2063* (2016.02); *A61B 2034/2065* (2016.02); *A61B 2505/05* (2013.01); *A61F 9/007* (2013.01); *G06T 2207/10012* (2013.01); *G06T 2207/30041* (2013.01)

(56) References Cited

U.S. PATENT DOCUMENTS

| | | | |
|---|---|---|---|
| 2012/0226150 | A1 | 9/2012 | Balicki et al. |
| 2014/0142591 | A1 | 5/2014 | Alvarez et al. |
| 2014/0221822 | A1 | 8/2014 | Ehlers et al. |
| 2014/0364870 | A1 | 12/2014 | Alvarez et al. |
| 2015/0077528 | A1 | 3/2015 | Awdeh |
| 2015/0141801 | A1* | 5/2015 | Jean .................... A61F 9/00736 600/411 |
| 2015/0173644 | A1* | 6/2015 | Ren ........................ A61B 5/066 600/424 |
| 2015/0173846 | A1* | 6/2015 | Schneider .......... A61B 1/00009 600/424 |
| 2015/0335480 | A1 | 11/2015 | Alvarez et al. |

OTHER PUBLICATIONS

An 11-page Extended European Search Report (EESR) for European patent application No. 16881397.0; the EESR was mailed from the European Patent Office (EPO) dated Jul. 12, 2019; European patent application No. 16881397.0 was filed at the EPO as a regional phase application from PCT/IL2016/051370.

* cited by examiner

SYSTEM AND METHOD FOR DETERMINING THE POSITION AND ORIENTATION OF A TOOL TIP RELATIVE TO EYE TISSUE OF INTEREST

FIELD OF THE DISCLOSED TECHNIQUE

The disclosed technique relates to system and method for preventing rapture of eye tissue of interest in general, and to systems and methods for determining the position and orientation of a tool tip relative to eye tissue of interest, in particular.

BACKGROUND OF THE DISCLOSED TECHNIQUE

The optical structure of the eye includes thin and fragile transparent tissues such as the cornea, the iris, the lens and the lens capsule. Common surgery procedures in ophthalmology (e.g., cataract surgery, IOL placement, cornea implantation and the like) are related to the front eye and are performed using a stereoscopic microscope. In general, the eye tissues are transparent and therefore difficult to see. These surgical procedures are complicated due to low visibility through the transparent eye tissues. During these procedures the surgeon needs to cut or avoid cutting these transparent tissues. Damage to transparent eye tissues might cause complication during the surgery, resulting long period of patient recovery, altering the outcome of the procedure and causing repeated surgeries and retirements. When the surgeon experiences difficulties in making accurate incision and procedures using the microscope, the procedure may not provide the desired results.

Prior art systems employ non-visual scanning technologies for locating the eye capsule during surgery. Reference is now made to U.S. Pat. No. 8,945,140 issued to Hubschman et al., and entitled "Surgical Procedures Using Instrument to Boundary Spacing Information Extracted from Real-Time Diagnostic Scan Data". This publication relates to a surgical method for providing a surgeon with additional guidance concerning the distance separating a working end of an instrument and the posterior capsule of the eye during a surgical procedure. The method involves acquiring non-visual three-dimensional data (i.e., diagnostic scan data), and processing the scan data for determining the distance between an instrument and the posterior boundary of the lens tissue. Visual and/or auditory conveyance of distance information is provided to the surgeon.

SUMMARY OF THE PRESENT DISCLOSED TECHNIQUE

It is an object of the disclosed technique to provide a novel method and system for determining the position and orientation of a tool tip relative to an eye tissue of interest. In accordance with one aspect of the disclosed technique, there is thus provided a system for determining the position and orientation of a tool tip relative to an eye tissue of interest. The system includes and imaging and tracking module and a processor. The processor is coupled with the imaging and tracking module. The imaging and tracking module at least includes an imager. The imager acquires at least one image of at least one tissue reference marker. The imaging and tracking module further determines information relating to the position and orientation of the tool. The processor determines, continuously and in real-time, the position and orientation of the tissue reference marker according to the acquired at least one image of the tissue reference marker. The processor determines the position and orientation of the eye tissue of interest, continuously and in real-time, according to the position and orientation of the tissue reference marker, and a predetermined relative position and orientation between the tissue reference marker and the eye tissue of interest. The processor also determines the position and orientation of a tool tip according to a tool marker and determines the relative position and orientation between the tool tip and the eye tissue of interest.

In accordance with another aspect of the disclosed technique, there is thus provided a method for determining the position and orientation of a tool tip relative to an eye tissue of interest. The method includes the procedures of acquiring at least one image of the of at least one reference marker in a reference coordinate system, determining, continuously and in real-time, the position and orientation of the at least one tissue reference marker in the reference coordinate system. The method also includes the procedure of determining the position and orientation of the eye tissue of interest in the reference coordinate system, continuously and in real-time, according to the position and orientation of the tissue reference marker, and a predetermined relative position and orientation between the tissue reference marker and the eye tissue of interest. The method further includes the procedure of determining the location and orientation of the tool tip in the reference coordinate system and determining the distance between the tool tip and the eye tissue of interest.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a system and a method for determining the position of a tool tip relative to eye tissue of interest. Accordingly, an imager acquires at least one image of the eye and specifically of the conjunctiva, iris, cornea and the transparent tissues. The acquired image or images include a representation of a tissue reference marker or markers (e.g., the iris, a fiducial marker or markers, blood vessels). A processor determines, continuously and in real-time, the position and orientation (abbreviated herein 'P&O') of the tissue reference marker or markers in a reference coordinate system. Also, the relative P&O between the eye tissue of interest and the tissue reference marker or markers is predetermined. The processor determines, continuously and in real-time, the P&O of the eye tissue of interest in the reference coordinate system, at least according to two factors. The first factor is the relative P&O between the eye tissue of interest and the tissue reference marker or markers and the second factor is the P&O of the tissue reference marker. The P&O of the eye tissue of interest in the reference coordinate system defines a maneuvering space in which the tool can be maneuvered without causing undesired damage to the tissue (i.e., which may or may not take into account safety distance thresholds). A tool tracker tracks (i.e., determines information relating to the P&O) the tool in the reference coordinate system. The processor determines the distance between the tool tip and eye tissue of interest and provides this determined distance to a distance indicator. The distance indicator produces an indication relating to the distance between the tool tip and the eye tissue of interest. The system and method according to the disclosed technique aids surgeons or others in preventing of undesired damage to the eye tissue incision and specifically to transparent tissue.

The term 'in real-time' herein above and below refers to operations (e.g., image acquisition, P&O determination) performed at a substantially high rate with regards to the system requirements (e.g., greater than 15 times per second) and at a substantially low latency relative to the system requirements (e.g., shorter than 0.1 seconds). The term 'continuously' herein above and below relates to repeatedly performing an operation (e.g., image acquisition, P&O determination) during a defined period of time.

Reference is now made to FIGS. 1A-1D, which are schematic illustrations of an exemplary system, generally referenced 100, for determining the P&O of a tool tip relative to eye tissue of interest, constructed and operative in accordance with an embodiment of the disclosed technique. Exemplary system 100 is described herein where the eye tissue of interest in the lens capsule and the tissue reference marker is the iris. System 100 includes a three dimensional (3D) imager 102, a processor 104, a distance indicator 106 and a database 108. Processor 104 is coupled with 3D imager 102, with distance indicator 106 and with database 108.

Figure 1A:
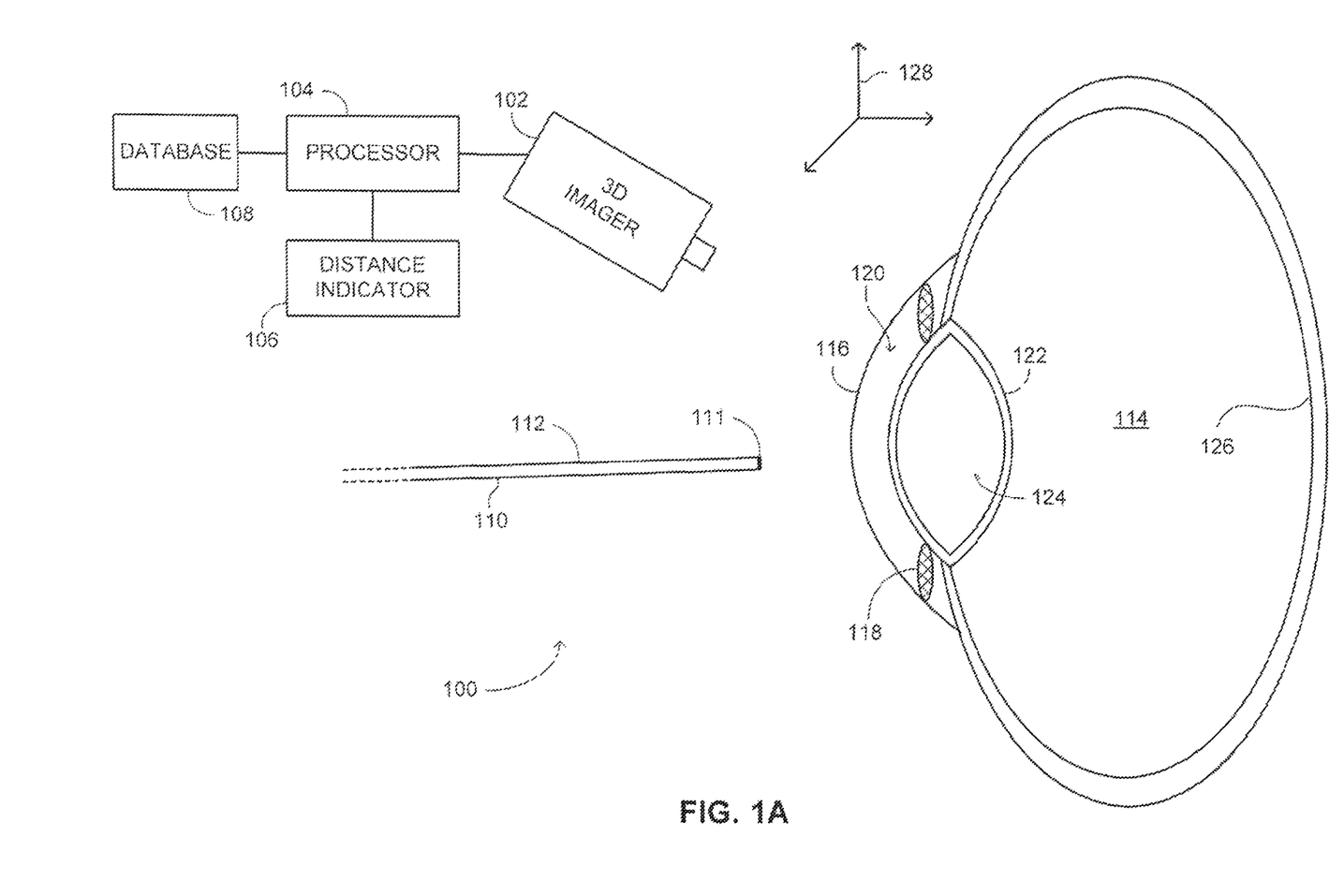
FIGS. 1A-1D are schematic illustrations of an exemplary system for determining the position and orientation of a tool tip relative to eye tissue of interest, constructed and operative in accordance with an embodiment of the disclosed technique.

3D imager 102 is, for example a stereoscopic imager, a structured light imager a Time-Of-Flight (TOF) imager and the like. Tool 110 includes a tool marker 112 which may be an active marker or a passive marker. An active marker is, for example, a light emitter (e.g., Light Emitting Diode— LED) emitting light at a wavelength to which 3D imager 102 is sensitive (i.e., 3D imager 102 can acquire images of tool marker 112 and tool marker 112 is identifiable in these images). A passive marker is, for example, a reflector (i.e., a specular reflector, a retro reflector or a diffusive reflector) reflecting light impinging thereon toward 3D imager 102.

System 100 is employed for tracking (i.e., determining the P&O) of a tool 110 and specifically of the tool top 111, relative to the anatomy of an eye 114 in general and to eye tissue of interest in particular. To that end, system 100 determines the P&O of tool marker 112 in a reference coordinate system 128 according to the images thereof acquired by 3D imager 102. Since the P&O of tool tip 111 relative to marker 112 is predetermined, system 100 determines the P&O of the tool tip 111.

Before describing the functionality of system 100, the following paragraph provides a brief description of eye 114. Eye 114 includes a cornea 116, an iris 118, an anterior chamber 120, a lens capsule 122, a lens 124, and a retina 126. Cornea 116 is a transparent front part of eye 114 that covers iris 118 and anterior chamber 120. Cornea 116 with anterior chamber 120, lens 124, refract light onto retina 126. Iris 118 is a thin circular structure responsible for controlling the diameter and size of a pupil (not shown) and thus the amount of light reaching retina 124. That is, iris 118 is the aperture stop and the pupil is the aperture. Anterior chamber 120 is a space between iris 118 and the inner surface of cornea 116, filled with aqueous humor. Lens capsule 122 is a clear (i.e., transparent), membrane structure, which completely surrounds lens 124. Lens capsule 122 assists shaping lens 124 and the surface curvature thereof. Lens 124 is a transparent, biconvex structure that helps (along with cornea 110) to focus light passing there through on retina 126. Retina 126 is the inner coat of the globe of eye 114, and is a light-sensitive layer of tissue.

Database 108 stores information relating to the relative P&O between an iris and a lens capsule. This relative P&O is substantially constant. Database 108 may further store information relating to the shape and size of a lens capsule. This stored information is employed to define a volumetric model of a lens capsule. During a procedure, 3D imager 102 continuously acquires 3D images of iris 118. 3D imager 102 provides the acquired 3D images to processor 104. Processor 104, determines, continuously and in real-time, the P&O of iris 118 in reference coordinate system 128 according to the acquired images. Processor 104 then determines, continuously, in real-time, the P&O of lens capsule 122 in reference coordinate system 128, according to determined P&O of iris 118 and according to the relative P&O between an iris and a lens capsule model stored in database 108. Thus, processor 104 determines an allowed maneuvering space in which the tool 110 can be maneuvered 110 without causing undesired damage to the tissue.

When either tool 110 or another tool (i.e., which is also fitted with a marker similar to tool marker 112) is inserted into lens capsule 122 (i.e., either manually or automatically), 3D imager 102 acquires real-time images of tool marker 112 and provides the acquired real-time images to processor 104. Processor 104 determines the P&O of the tool tip 111 in reference coordinate system 128 in real-time. Then, processor 104 determine the distance between the tool tip 111 and lens capsule 122 and provides this determined distance to distance indicator 106. This distance is, for example, the smallest distance to lens capsule 122 or the distance between tool tip 111 and lens capsule 122 in the direction in which tool tip 111 is oriented. Distance indicator 106 produces an indication relating to the distance between the tool tip 111 and the boundaries of lens capsule 122.

The indication produced by distance indicator 106 may be a visual indication such as a numerical representation of the distance, distance bars and the like. As a further example, the visual indication may be presented on a display (e.g., a LCD screen, Heads-Up-Display, Near-To-Eye display and the like). The visual indication may also be a 3D model (i.e., either the above mentioned stored model or a different model) of the eye along with a symbol of tool 110. The P&O of the symbol of tool 110 on the display, relative to the position of the 3D model of the eye corresponds to the relative P&O between tool 110 and lens capsule 122. The visual indication may further include a flashing symbol, where the flashing frequency is inversely proportional to the distance between tool tip 111 and the lens capsule 122. The indication may be alternatively or additionally be an audio indication such as a sound with a pitch or volume or both, which varies according to the distance. The sound can be also of voice indicating the distance or warning following the distance to the capsule. As a further alternative or in addition, distance indicator 106 may indicate that the distance between the tool tip 111 and lens capsule 122 is below a threshold. In the example brought forth hereinabove, the processor determines the entire lens capsule 122 as the maneuvering space in which the tool 110 can be maneuvered 110 without causing undesired damage to the tissue (i.e., without taking into account safety thresholds). However, this maneuvering space may be further limited (i.e., taking into account safety thresholds). For example, with reference to FIG. 1D, processor 104 may defines a virtual boundary 130 relating to lens capsule 124 or a portion thereof. This virtual boundary further limits the maneuvering space in which the user may maneuver tool 110 without causing undesired damage to the tissue. When tool 110 crosses that virtual boundary, an indication is produced as described above. This virtual boundary may also be displayed to the user as part of the above mentioned 3D model.

As mentioned above, tool 110 may move automatically. For example, tool 110 is attached to a robot (not shown), such a robotic arm, which is coupled with processor 104. Processor 104 instructs the robot to move tool 110 toward lens capsule 122 according to the P&O of tool 110 and of lens capsule 122. Processor 104 may further instruct the robot to stop, for example, when the distance between the tool tip 111 and lens capsule 122 is below a threshold.

Figure 1B:
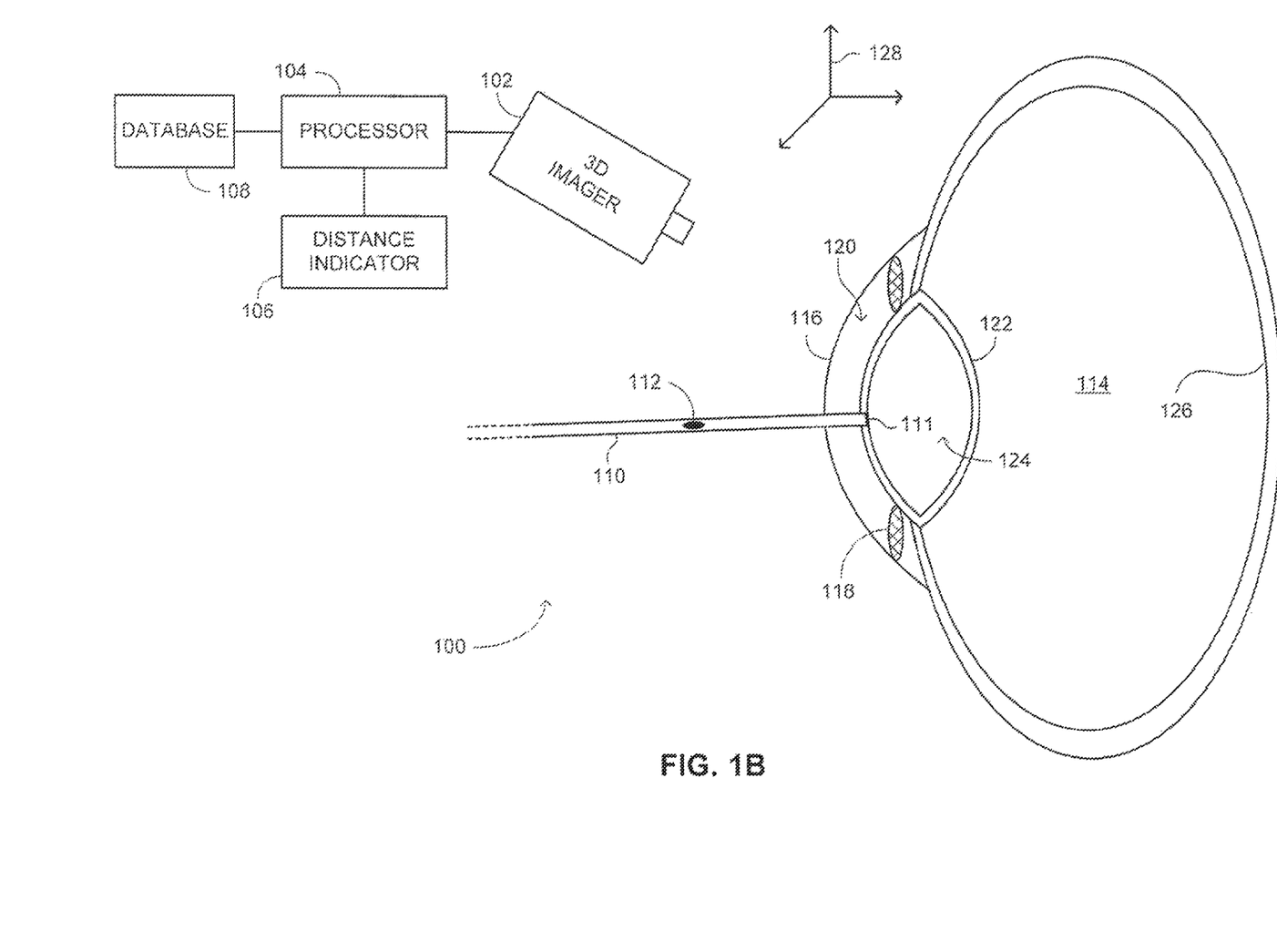
Figure 1C:
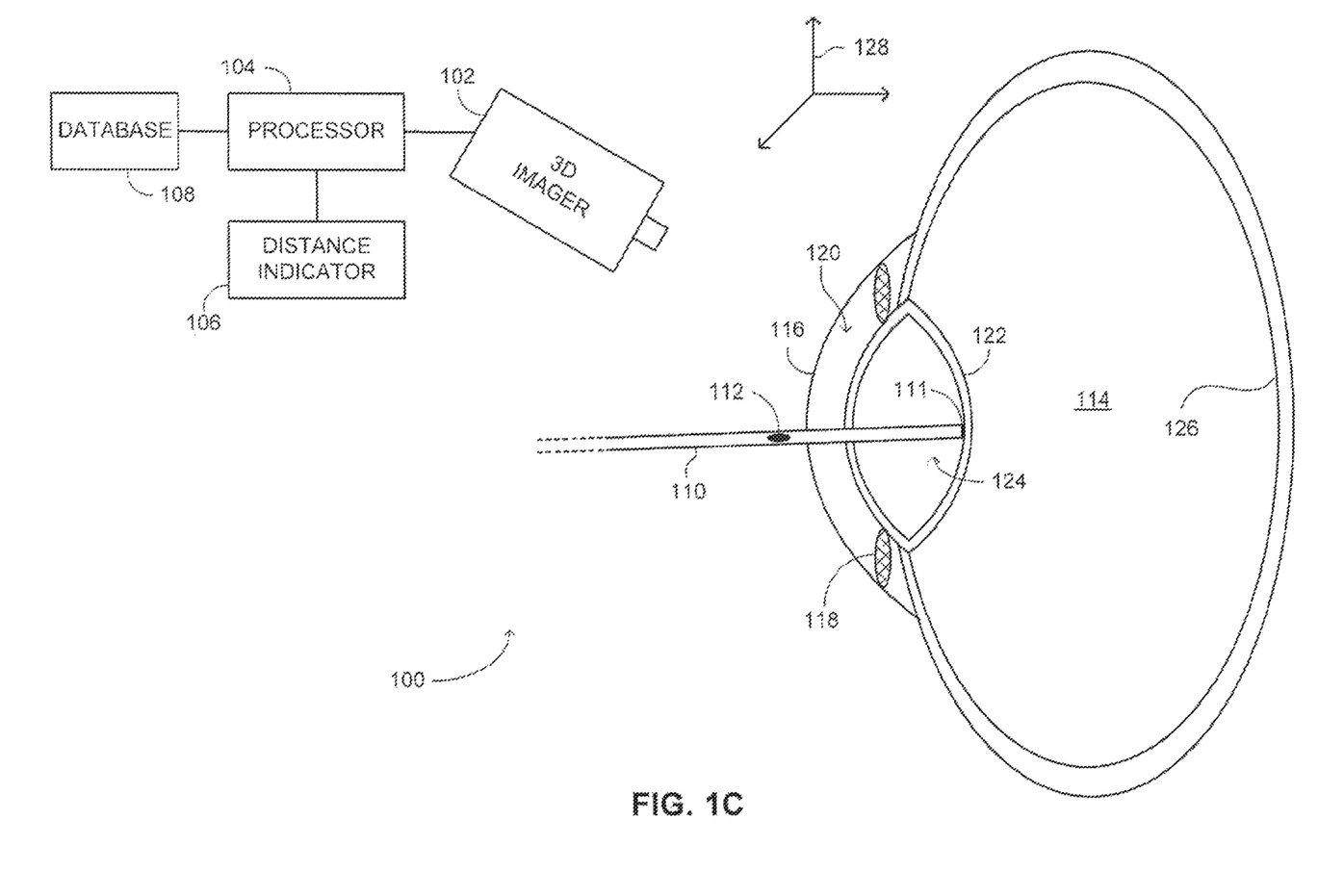
Figure 1D:
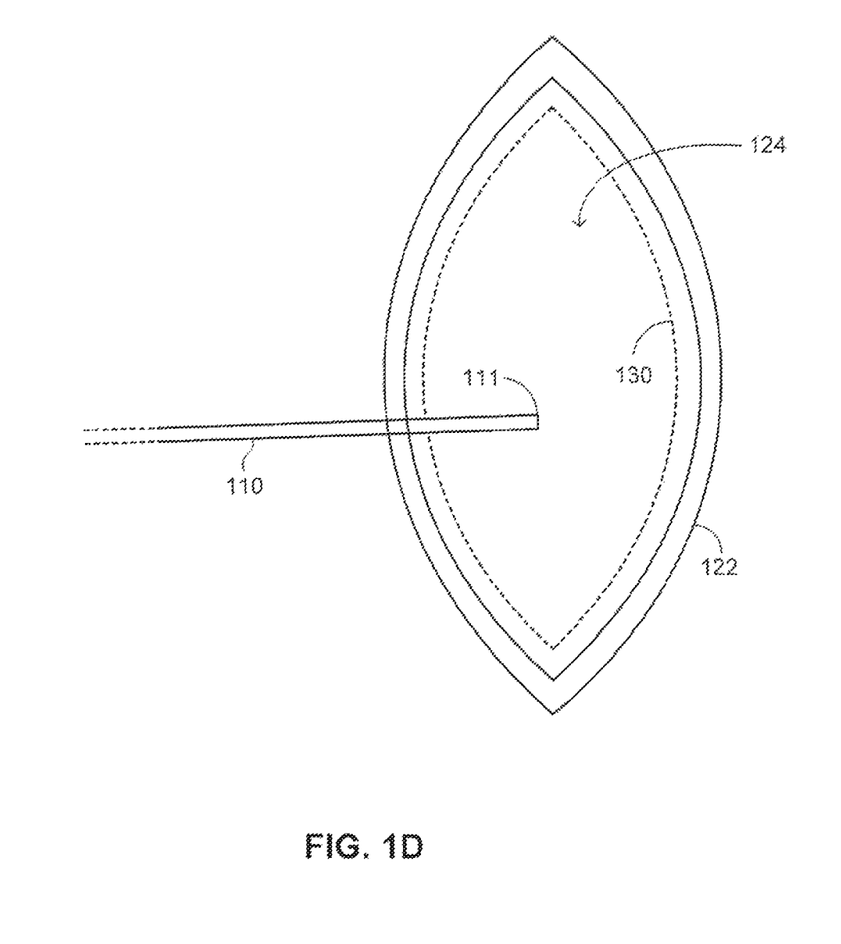

The accuracy of the above mentioned estimation of P&O, the geometrical structure and the size of lens capsule 122 in reference coordinate system 128 (i.e., the accuracy of the volumetric model), may be improved (i.e., conform more closely to the actual values) by acquiring information relating to the actual P&O of lens capsule 122. To that end, and with reference to FIG. 1B, tool 110 moves. 3D imager 102 acquires a respective 3D image or images of tool marker 112, when tool tip 111 is in contact or in close to contact with the outer boundary of lens capsule 122, at one or more point (e.g., as determined by looking at tool tip 111 through a microscope). 3D imager 102 provides the acquired image to processor 104. With reference to FIG. 1C, tool 110 continues to move. 3D imager 102 acquires another respective 3D image or images of tool marker 112, when tool tip 111 is in contact or in close to contact with the inner boundary of lens capsule 122, at one or more point. Processor 104 determines the positions and optionally the orientations of tool tip 111 in reference coordinate system 128, when tool tip 111 is in contact or in close contact with outer and inner boundaries points of lens capsule 122. According to the determined positions and/or orientation of tool tip 111, processor 104 determines a model of lens capsule 122 by estimating the geometrical structure and the size of lens capsule 122 as well as the P&O of lens capsule 122 in reference coordinate system 128. For example, when only two points are employed (i.e., one on the outer boundary and one in the inner boundary of lens capsule 122) then processor 104 determines an approximation of the width of lens capsule 122. Nevertheless, determining the positions and orientations of tool tip 111, when tool tip 111 is in contact or in close contact with outer and inner boundaries of lens capsule 122 at more than one point increases the accuracy of the above mentioned estimation of the geometrical structure, the size, the position and the orientation of lens capsule 122.

When determining the P&O of lens capsule 122 in real-time, processor 104 may further employ the above mentioned positions of tool tip 111, when tool tip 111 is in contact or in close contact with outer and inner boundaries of lens capsule 122, to improve the accuracy of the determined P&O of lens capsule 122 (e.g., by employing the locations of these boundary points as constraints). According to another alternative, modeling lens capsule 122 prior to the procedure may be achieved by employing imaging techniques. For example, prior to the procedure an Optical Coherence Tomography (OCT) image or an ultrasound image of the eye is acquired (i.e., a model image). This image includes a representation of lens capsule 122. The geometrical structure and the size of lens capsule 122 may be derived from such images by employing image processing techniques. Also the relative P&O between the iris 118 and lens capsule 122 may be determined from the acquired images when both lens capsule 122 and the iris 118 are visible in the model image. It is noted that in general, modeling lens capsule 122 and determining the P&O of iris 118 may be done sequentially or concurrently.

As described above, processor 104 employs iris 118 as tissue reference marker and determines the P&O of the iris 118 in reference coordinate system 128. However, the tissue reference marker may be any marker detectable by 3D imager 102, where the relative P&O between the lens capsule 122 and the marker is predetermined. For example, the tissue reference marker may be conjunctiva, blood vessels within the conjunctiva or within other organs of the eye. Alternatively, the tissue reference marker can be an artificial marker (e.g., fiducial marker) placed on the eye. For example, the tissue reference marker is patch attached to lens capsule 122 when the boundaries of lens capsule 122 are determined. As a further example, the tissue reference marker is drawn on the eye by a dedicated marker pen. To determine the P&O of the tissue reference marker in the acquired 3D image, processor 104 employs image processing techniques. For example, when the tissue reference marker is iris 118, processor 104 identifies the iris in the acquired 3D image by identifying a black circle which relates to the pupil encircled by a first ring, which relates to the iris, encircled by a second ring which relates to the limbus. Thus, the iris pattern and shape provide a discernible tissue reference marker for the system. The P&O of the first ring relates to the position of iris 118.

Figure 2:
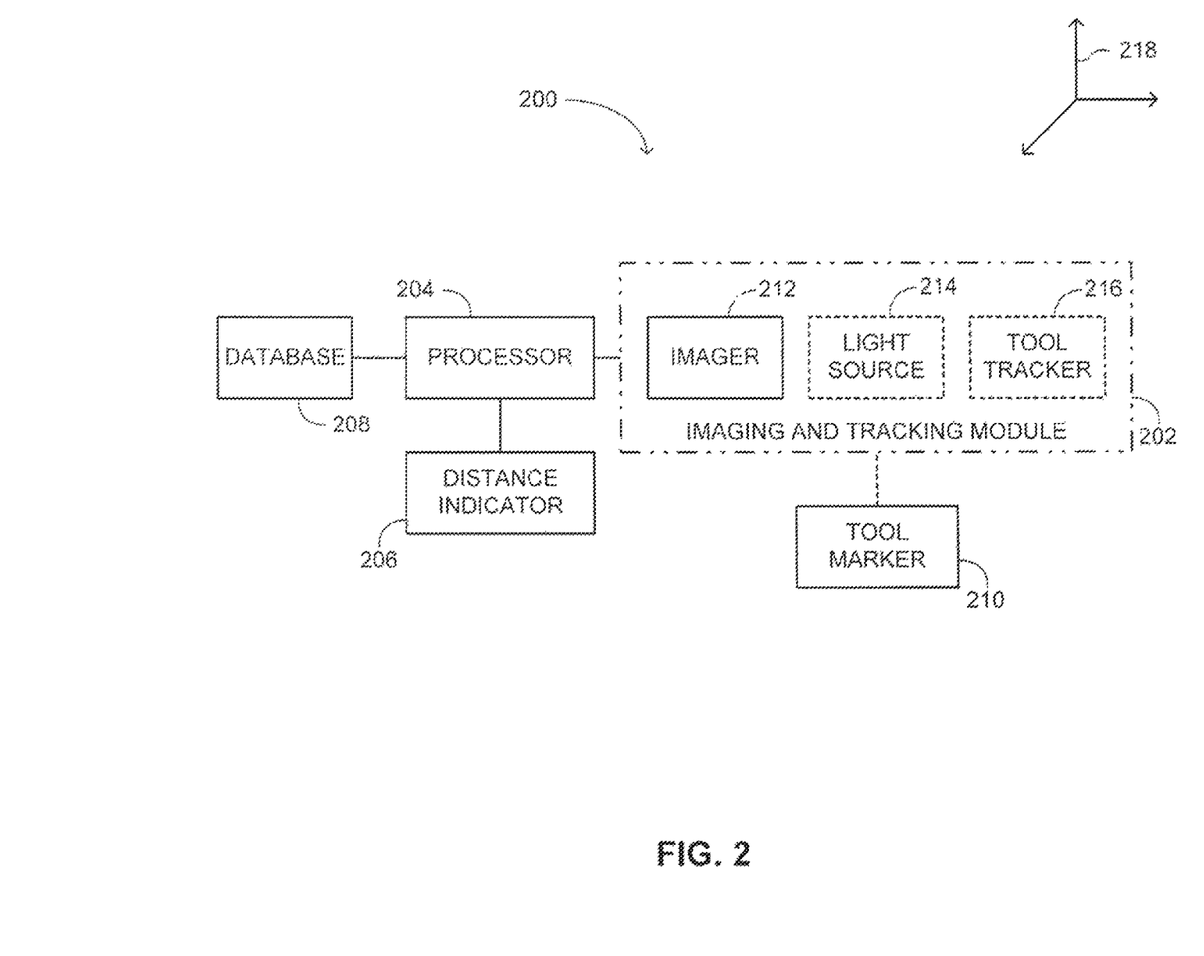
FIG. 2 is a schematic illustration of system for determining the position and orientation of a tool tip relative to eye tissue of interest, constructed and operative in accordance with another embodiment of the disclosed technique.

The system described herein above in conjunction with FIGS. 1A-1C relates to an exemplary system in which a 3D imager is employed for imaging as well as for tracking and where the eye tissue of interest is the lens capsule and the tissue reference marker is the iris. In general, a system according to the disclosed technique may employ various techniques for tracking a medical tool such as optical tracking, electromagnetic tracking, ultrasound tracking and inertial tracking. Furthermore, as mentioned above, the 3D imager may be any one of various 3D imagers such as stereoscopic camera, structured light imager or a TOF camera. Alternatively, the imager may be a two dimensional (2D) imager. When the imager is a 2D imager at least three artificial markers are placed on the eye. Also the eye tissue of interest may be other tissues in the eye, for example, the retina. Reference is now made to FIG. 2, which is a schematic illustration of a system, generally referenced 200, for determining the P&O of a tool tip relative to the eye tissue of interest, constructed and operative in accordance with another embodiment of the disclosed technique. The operation of system 200 is similar to the operation of system 100 described above in conjunction with FIGS. 1A-1C. System 200 includes an imaging and tracking module 202, a processor 204, a distance indicator 206, and database 208 and a tool marker 210. Imaging and tracking module 202 at least includes an imager 212. Imager 212 may be a 3D imager or a 2D imager. Imaging and tracking module 202 optionally includes a light source 214 and a tool tracker 216 (i.e., as indicated by the hatched lines). Processor 204 is coupled with imaging and tracking module 202, with distance indicator 206 and with database 208. Tool marker 210 is coupled with imaging and tracking module 202.

When imager 212 is a 3D imager, imager 212 acquires a 3D image of the eye. The term '3D image' relates herein above and below relates to image data which includes information relating to the P&O (i.e., in a reference coordinate system) of the various features in the scene. When imager 212 is a 3D imager, imager 212 may be embodied as a stereoscopic camera, which acquires two images of the eye from two different perspectives. When imager 212 is a stereoscopic camera, light source 214 is optional. Imager 212 may alternatively be embodied as a structured light imager. In such a case, light source 214 illuminates the eye with structured light and imager 212 acquires an image (i.e., may be a two-dimensional image) of the illuminated eye (i.e., with the structured light). According to another alternative, imager 212 may be a TOF camera. Accordingly, light source 214 emits temporal pulse of light toward the eye. Imager 212 is time synchronized with light source 214 and acquires an image or images of the eye. Imager 12 integrates light only when the light pulse is expected to reflect back to the imager. The difference between the time light source 214 emits a pulse and the time imager 212 acquires an image of the reflected light pulse is related to the distance between imager 212 to tracking module 202 and the object being tracked. When imager 212 is a 2D imager, imager 212 acquires a 2D image or images of at least three artificial tissue reference markers placed on the eye. The relative positions between the artificial markers are known (e.g., stored in database 208 when a relatively high degree of accuracy is require). Alternatively, the relative positions between the markers are determined, for example, by placing the tool tip on each marker, determining the position of each marker in reference coordinate system 218 and determining the relative positions between the markers accordingly.

In general, tool tracker 216 at least acquires information relating to the P&O of tool marker 210 in reference coordinate system 218. According to one alternative, similar to as described above in conjunction with FIG. 1A-1C, tool tracker 216 and imager 212 are one and the same. Accordingly, similar to as described above, tool marker 210 is an active or a passive marker. For example, tool marker 210 is an array of LEDs or fiducial markers located on the tool and identifiable in an image acquired by imager 212. Tool marker 210 is thus considered to be optically coupled with imaging and tracking module 202 and the P&O tool marker 210 is determined according to the images acquired by imager 212. According to another alternative, tool tracker 216 is an optical tracker different from imager 212. In both cases the information relating to the P&O of tool marker 210 are images of tool marker 210. Tool tracker 216 may also track the tool according to the shape thereof. The shape of the tool maybe stored in database 208 based on a tool model acquired during a preliminary learning stage of system 200. Accordingly, imager 212 acquires 3D image of the tool.

According to a further alternative, tool tracker 216 is an electromagnetic tracker and tool marker 210 is at least one electromagnetic sensor (e.g., coils, Hall Affect sensors). Tool marker 210 is thus considered to be electromagnetically coupled with imaging and tracking module 202 and the P&O of tool marker 210 is determined according to the measurements of a magnetic field by the electromagnetic sensors. The electromagnetic is generated by tool tracker 216.

According to yet another alternative, tool tracker 216 is an ultrasonic tracker and tool marker 210 includes at least one ultrasonic transducer and tool tracker 216 includes at least three ultrasonic receivers. Tool marker 210 is thus considered to be ultrasonically coupled with imaging and tracking module 202 and the P&O of tool marker 210 is determined according to the measurements of a the time elapsed between the transmission and reception of the sound and the velocity of sound in the medium.

According to yet another alternative, tool tracker 216 is an inertial navigation system and tool marker 210 is an Inertial Measurement Unit (IMU). Tool marker 210 provides information regarding the linear and rotational accelerations of the tool and tool tracker determines the P&O of tool marker 210 accordingly relative to an initial known reference.

According to one embodiment, processor 204 determines the P&O of tool marker 210 according to information relating to the P&O of tool marker 210 provided by tool tracker 216. Alternatively, tool tracker 216 determines the P&O of tool marker 210 and provides the determined P&O to processor 204. In both cases, processor 204 determines the P&O of the tool tip and the distance between the tool tip and the eye tissue of interest.

Processor 204 includes component required for performing computing operations, such as a central processing unit that may be implemented with a conventional microprocessor, a random access memory (RAM) for temporary storage of information, and a read only memory (ROM) for permanent storage of information. A memory controller is provided for controlling RAM. A bus interconnects the components of the processor system. A bus controller is provided for controlling the bus. An interrupt controller is used for receiving and processing various interrupt signals from the system components. Mass storage may be provided by a Hard Disc Drive (HDD) or by a flash drive. The processor system further includes a network interface that allows the system to be interconnected to a local area network (LAN) or a wide area network (WAN). Operation of the processor is generally controlled and coordinated by operating system software that can be stored on the memory. Processor 204 provides this determined to distance indicator 206. Distance indicator 206 provides an indication of the distance between the tool tip and the eye tissue of interest similar to as described above.

During a procedure, imager 212 continuously acquires images of the tissue reference marker or markers. Imager 212 provides the acquired images to processor 204. The acquired images include information relating the position and orientation of the tissue reference marker or markers. For example, when imager 212 is a stereoscopic camera, the relation between the position of an image-feature in an image acquired by one camera, and the position of the same image-feature in an image acquired by the second cameral, is associated with the position of the actual feature in reference coordinate system 218. By identifying the image-features associated with the tissue reference marker or markers, the position and orientation thereof, in reference coordinate system 218 may be determined. When imager 212 is a 2D imager, imager 212 acquires an image of at least three artificial markers. The image pixel location of each marker is associated with two angles (i.e., a horizontal angle and a vertical angle measured from the center of the imaging sensor). In essence, these angles, along with the known, relative position between the tissue reference markers, define six equations with six unknowns (i.e., three for position and three for orientation). Thus, processor 204, continuously and in real-time, determines the P&O of the tissue reference marker in a reference coordinate system 218 according to the acquired images. Processor 204 then determines, continuously and in real-time, the P&O of the eye tissue of interest in reference coordinate system 218, according to determined P&O of the tissue reference marker and according to the stored relative P&O between tissue reference marker or markers and the eye tissue. Thus, processor 204 determines a maneuvering space in which the user may maneuver tool 110 in which the tool can be maneuvered without causing undesired damage to the tissue (i.e., which may or may not take into account safety distance thresholds).

Processor 204 determines the P&O of the tool tip in real-time and determines the distance between the tool tip and the eye tissue of interest. Processor 204 provides this determined to distance indicator 206. Distance indicator 206 provides an indication of the distance between the tool tip and the eye tissue of interest similar to as described above. Similar to system 100, a maneuvering space in which the user may maneuver tool 110 in which the tool can be maneuvered without causing undesired damage to the tissue take into account safety distance thresholds, for example, by defining a virtual boundary relating to the eye tissue of interest. When the tool crosses that virtual boundary, an indication is produced a described above.

The accuracy of the estimation of the geometrical structure, the size, the position and the orientation of eye tissue of interest in reference coordinate system 218, may be improved by modeling the eye tissue prior to the procedure. To that end, processor 204 employs the positions of tool tip, when the tool tip is in contact or in close contact with the eye tissue of interest at more than one point. According to another alternative, modeling the eye and the eye tissue of interest prior to the procedure may be achieved by employing imaging techniques. For example, prior to the procedure an Optical Coherence Tomography (OCT) image or an ultrasound image of the eye is acquired (i.e., a model image). This model image includes a representation of the eye tissue of interest. The geometrical structure and the size of the eye tissue of interest may be derived from such images by employing image processing techniques. When the eye and the eye tissue of interest with imaging techniques and the relative P&O between the tissue reference marker (i.e., either anatomical or biological) and the eye tissue of interest may be determined from the acquired images when both the eye tissue of interest and the tissue reference marker are visible in the model image.

As mentioned above, the eye tissue of interest may be the retina. In such a case, the reference marker is preferably a fiducial marker and the P&O of the retina is calculated relative thereto. Processor 204 determines the P&O of the tool tip in real-time and determines the distance between the tool tip and the retina. Processor 204 provides this determined distance to distance indicator 206. Distance indicator 206 provides an indication of the distance between the tool tip and the eye tissue of interest similar to as described above.

Figure 03:
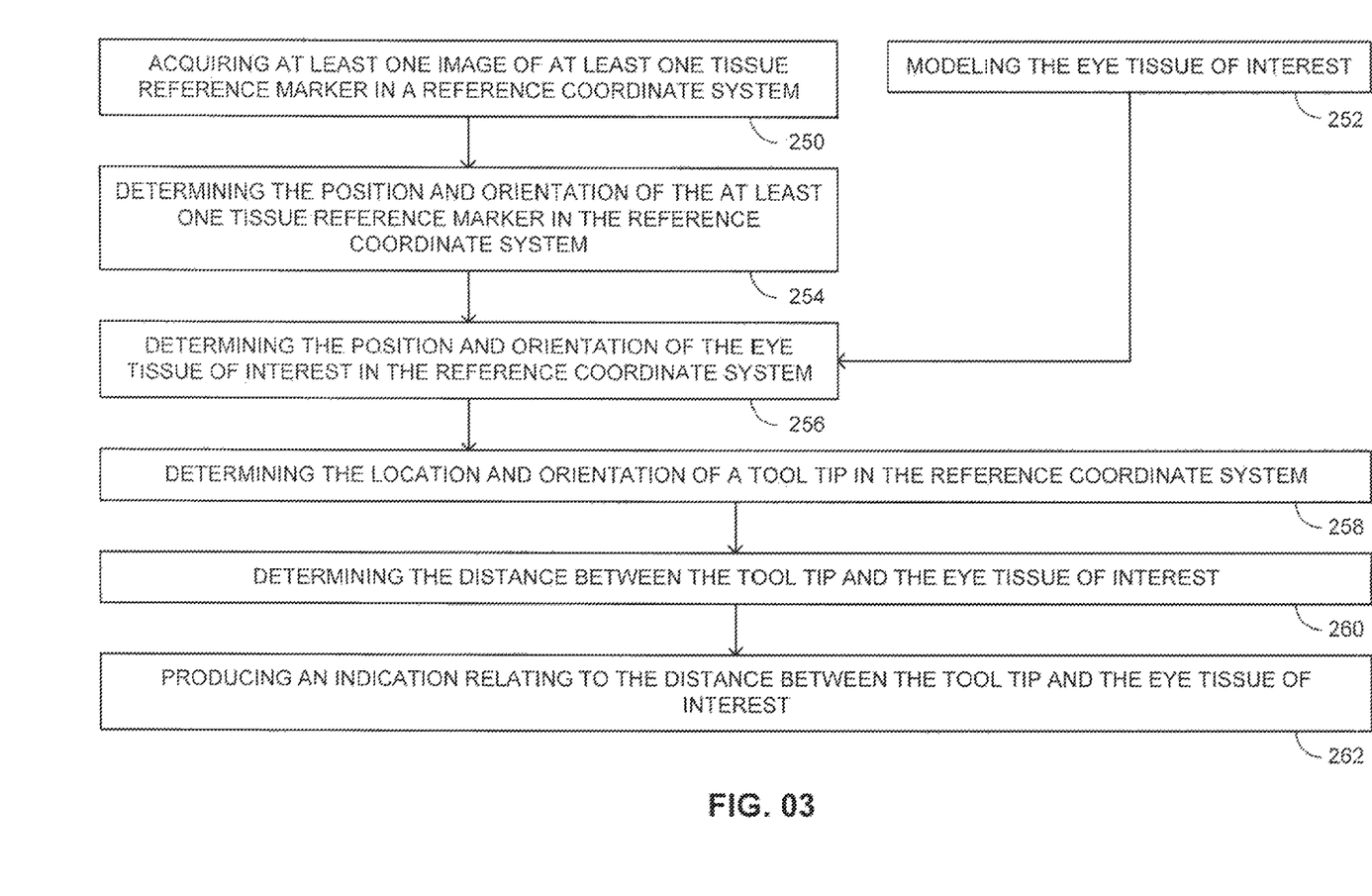
FIG. 3 is a schematic illustration of method for determining the position and orientation of a tool tip relative to eye tissue of interest, operative in accordance with a further embodiment of the disclosed technique.

Reference is now made to FIG. 3, which is a schematic illustration of a method for determining the position and orientation of a tool tip relative to the an eye tissue of interest, operative in accordance with a further embodiment of the disclosed technique. In procedure 250, at least one image of at least one tissue reference marker are acquired in a reference coordinate system. The image or images may be 2D images or 3D images. The 3D images may be a stereoscopic image, a structured light image or a TOF image. When the image or images are 2D images, at least three tissue reference markers are employed. With reference to FIG. 2, imager 212 acquires an image of at least one tissue reference marker. After procedure 250, the method proceeds to procedure 254.

In procedure 252, the eye tissue of interest is modeled. The eye tissue of interest is modeled, for example, improving the accuracy of a priori information relating to estimations of the P&O, the geometrical structure and the size of the eye tissue of interest, by determining position, and optionally the orientation of the tool tip when the tool tip is in contact or in close contact with points on the tissue. Alternatively, the eye tissue of interest is modeled by employing imaging such as OCT or ultrasound imaging. For example, With reference to FIGS. 1A-1C and 2, processor 204 determines a model of the eye tissue of interest. To that end, tool 110 moves. Tool tracker 216 acquires information relation to the position of the tool tip when the tip of tool is in contact or close contact with the eye tissue of interest at one or more points and provides the acquired information to processor 204. Processor 204 determines a model of lens the eye tissue of interest by estimating the geometrical structure and the size thereof, as well as the P&O in a reference coordinate system 218. After procedure 252 the method proceeds to procedure 256. Also, it is noted that procedure 252 is optional.

In procedure 254, the P&O of a tissue reference marker or markers is determined in the reference coordinate system. The P&O of the at least one tissue reference marker is determined, continuously and in real-time according to the acquired image or images thereof. The tissue reference marker may be an anatomical marker such as the iris. However, the tissue reference marker or markers may also be the conjunctiva, blood vessels within the conjunctiva or within other organs of the eye. Alternatively, the tissue reference marker or markers may be artificial markers placed on the eye such as a patch attached, fiducial markers or a dedicated pen markers drawn on the eye. With reference to FIG. 2, processor 204 determines the P&O of a tissue reference marker in reference coordinate system 218.

In procedure 256, the P&O of the eye tissue of interest is determined in the reference coordinate system. The P&O of the eye tissue of interest is determined, continuously and in real-time, according to P&O of the tissue reference marker or markers and according to the predetermined relative P&O between the tissue reference marker or markers and the eye tissue of interest. Thus, a maneuvering space is determined in which a tool can be maneuvered without causing undesired damage to the tissue (i.e., which may or may not take into account safety distance thresholds). With reference to FIG. 2, processor 204 determines the P&O of the eye tissue of interest. It is noted that procedure 254 is optional. After procedure 254, the method proceeds to procedure 258.

In procedure 258, the P&O of a tip of a tool is determined in the reference coordinate system. With reference to FIG. 2, tool tracker 216 acquires information relating to the P&O of the tool tip and processor 204 determines the P&O of the tool tip accordingly.

In procedure 260, the distance between the tool tip and the eye tissue of interest is determined. With reference to FIG. 2, processor 204 determines the distance between the tool tip and the eye tissue of interest.

In procedure 262, an indication relating to the distance between the tool tip and the eye tissue of interest is produced. This indication may be a visual indication such as a numerical representation of the distance or an array of Light Emitting Diodes, distance bars and the like. As a further example, the visual indication may be presented on a display (e.g., a LCD screen, an Heads-Up-Display, a Near-To-Eye display and the like) which shall display the determined 3D model of the eye along with a symbol the tool. The indication may be alternatively or additionally be an audio indication such as a sound with a pitch or volume or both, which varies according to the distance. As a further alternative or in addition, an indication is produced may indicate that the distance between the tool tip and the eye tissue of interest is below a threshold. With reference to FIG. 2, distance indicator 206 produces an indication relating to the distance between the tool tip and the eye tissue of interest.

It will be appreciated by persons skilled in the art that the disclosed technique is not limited to what has been particularly shown and described hereinabove. Rather the scope of the disclosed technique is defined only by the claims, which follow.

The invention claimed is:

1. A system for determining a position and orientation of a tool tip of a tool, relative to an eye tissue of interest, the system comprising:
   an imaging and tracking module, said imaging and tracking module at least including an imager, said imager configured to acquire at least one image of at least one tissue reference marker, said at least one tissue reference marker being different from said eye tissue of interest, said imaging and tracking module further configured to determine information relating to the position and orientation of said tool; and
   a processor coupled with said imaging and tracking module, said processor configured to determine, continuously and in real-time, the position and orientation of said at least one tissue reference marker according to the acquired at least one image of said at least one tissue reference marker,
   said processor configured to determine the position and orientation of said eye tissue of interest, continuously and in real-time, according to said position and orientation of said at least one tissue reference marker, and a predetermined relative position and orientation between said at least one tissue reference marker and said eye tissue of interest, said relative position and orientation between said at least one tissue reference marker and said eye tissue of interest is determined from a model of said eye,
   said processor configured to determine the position and orientation of said tool tip according to a tool marker, said processor further determining a relative position and orientation between said tool tip and said eye tissue of interest.

2. The system according to claim 1 further including a distance indicator, coupled with said processor, configured to provide an indication relating to a distance between said tool tip and said eye tissue of interest,
   wherein said distance indicator is a display configured to display a visual indication of said distance between said tool tip and said eye tissue of interest,
   wherein said visual indication is a three-dimensional model of the eye along with a symbol of said tool, and
   wherein, the position and orientation of said symbol on said display, relative to the position of said three-dimensional model of the eye corresponds to the relative position and orientation between said tool tip and said eye tissue of interest.

3. The system according to claim 2, wherein said display is one of a heads-up-display and a head-mounted-display.

4. The system according to claim 2, wherein said distance indicator provides an audio indication which varies according to the distance between said tool tip and said eye tissue of interest.

5. The system according to claim 1, wherein said imager is a three-dimensional imager.

6. The system according to claim 5, wherein said three-dimensional imager is a stereoscopic camera.

7. The system according to claim 5, wherein said three dimensional imager is a time-of-flight camera, and
   wherein, said imaging and tracking module further includes a light source configured to emit pulsed light.

8. The system according to claim 5, wherein said three-dimensional imager is a structured light camera, and
   wherein, said imaging tracking module further includes a light source configured to emit structured light.

9. The system according to claim 1, wherein said imager is a two dimensional imager,
   wherein said at least one tissue reference marker includes at least three artificial markers.

10. The system according to claim 1, wherein said at least one tissue reference marker is at least one of the group consisting of:
    the iris;
    the conjunctiva;
    blood vessels within the conjunctiva; and
    artificial marker.

11. The system according to claim 1, wherein said model is a volumetric model of said eye tissue of interest,
    wherein the accuracy of said volumetric model is improved by determining at least the position of said tool tip when said tool tip is at least in close contact with the eye tissue of interest at one or more point,
    wherein said volumetric model is determined by acquiring one of an Optical Coherence Tomography image and an ultrasound image of the eye is acquired.

12. The system according to claim 11, further including database coupled with said processor, said database storing said volumetric-model.

13. A method for determining a position and orientation of a tool tip of a tool relative to an eye tissue of interest, the method comprising the procedures of:
    acquiring at least one image of at least one tissue reference marker in a reference coordinate system, said at least one tissue reference marker being different from said eye tissue of interest;
    determining, continuously and in real-time, the position and orientation of said at least one tissue reference marker in said reference coordinate system;
    determining a position and orientation of said eye tissue of interest in said reference coordinate system, continuously and in real-time, according to said position and orientation of said at least one tissue reference marker, and a predetermined relative position and orientation between said at least one tissue reference marker and said eye tissue of interest, said relative position and orientation between said at least one tissue reference marker and said eye tissue of interest is determined from a model of said eye tissue of interest;
    determining a position and orientation of said tool tip in the reference coordinate system;
    determining a relative position and orientation between said tool tip and said eye tissue of interest from said position and orientation of said tool tip in the reference coordinate system and said position and orientation of said eye tissue of interest in said reference coordinate system; and determining a distance between said tool tip and said eye tissue of interest.

14. The method according to claim 13, further includes the procedure of producing an indication relating to the distance between the tool tip and said eye tissue of interest,
   wherein said indication is a visual indication of said distance,
   wherein said visual indication is a three-dimensional model of the eye along with a symbol of said tool tip,
   wherein, a displayed position and orientation of said symbol, relative to a displayed position of said three-dimensional model of the eye, corresponds to said relative position and orientation between said tool tip and said eye tissue of interest, and
   wherein said indication is an audio indication which varies according to the distance between said tool tip and said eye tissue of interest.

15. The method according to claim 13, further includes a preliminary procedure of modeling the eye tissue of interest.

16. The method according to claim 13, wherein said model is a volumetric model of said eye tissue of interest,
   wherein the accuracy of said volumetric-model is improved by determining at least the position of said tool tip when said tool tip is at least in close contact with the eye tissue of interest at more than one point, and
   wherein said volumetric model is determined by acquiring one of an Optical Coherence Tomography image and an ultrasound image of the eye is acquired.

17. The method according to claim 13, wherein said at least one image is a three dimensional image, and
   wherein said three dimensional image is one of a stereoscopic image, a time-of-flight image and a structured light image.

18. The method according to claim 13, wherein said at least one image is a three dimensional image.

19. The method according to claim 13, wherein said at least one tissue reference marker is at least one of a group consisting of:
   the iris;
   the conjunctiva;
   blood vessels within the conjunctiva; and
   artificial marker.

* * * * *